(12) United States Patent
Hata

(10) Patent No.: US 12,135,476 B2
(45) Date of Patent: Nov. 5, 2024

(54) MEDICAL OBSERVATION SYSTEM AND DISPLAY DEVICE

(71) Applicant: Sony Group Corporation, Tokyo (JP)

(72) Inventor: Kenji Hata, Tokyo (JP)

(73) Assignee: Sony Group Corporation, Tokyo (JP)

( * ) Notice: Subject to any disclaimer, the term of this patent is extended or adjusted under 35 U.S.C. 154(b) by 205 days.

(21) Appl. No.: 17/623,273

(22) PCT Filed: Jul. 17, 2020

(86) PCT No.: PCT/JP2020/027790
§ 371 (c)(1),
(2) Date: Dec. 28, 2021

(87) PCT Pub. No.: WO2021/020159
PCT Pub. Date: Feb. 4, 2021

(65) Prior Publication Data
US 2022/0357616 A1    Nov. 10, 2022

(30) Foreign Application Priority Data

Jul. 31, 2019 (JP) .................................. 2019-140678

(51) Int. Cl.
*G02F 1/1335* (2006.01)
*A61B 1/04* (2006.01)
(Continued)

(52) U.S. Cl.
CPC .......... *G02F 1/133502* (2013.01); *A61B 1/04* (2013.01); *G02B 1/118* (2013.01); *G02B 5/0236* (2013.01); *G02B 5/30* (2013.01)

(58) Field of Classification Search
None
See application file for complete search history.

(56) References Cited

U.S. PATENT DOCUMENTS

| 9,122,002 B2 | 9/2015 | Imaoku |
| 2008/0145609 A1 | 6/2008 | Lin |

(Continued)

FOREIGN PATENT DOCUMENTS

| JP | 2007-65563 A | 3/2007 |
| JP | 2007187868 A | 7/2007 |

(Continued)

OTHER PUBLICATIONS

International Search Report and Written Opinion mailed on Sep. 24, 2020, received for PCT Application PCT/JP2020/027790, Filed on Jul. 17, 2020, 12 pages including English Translation.

*Primary Examiner* — Shan Liu
(74) *Attorney, Agent, or Firm* — XSENSUS LLP

(57) ABSTRACT

A display device includes a display unit that displays a biological image and a transparent protective plate disposed on a front surface of the display unit. In the display device, an uneven structure having unevenness with a pitch and a height smaller than a wavelength of visible light is formed on any one or more of a front surface side of the protective plate, a back surface side of the protective plate, and a front surface side of the display unit, and an anti-glare (AG) structure having an AG function is formed on any one or more of the front surface side of the protective plate, the back surface side of the protective plate, and the front surface side of the display unit. The present technology can be applied to a display device that displays a biological image.

9 Claims, 22 Drawing Sheets

(51) Int. Cl.
*G02B 1/118* (2015.01)
*G02B 5/02* (2006.01)
*G02B 5/30* (2006.01)

(56) References Cited

U.S. PATENT DOCUMENTS

| | | |
|---|---|---|
| 2010/0195204 A1 | 8/2010 | Walker |
| 2011/0003121 A1* | 1/2011 | Tsuda ............... G02B 1/118 |
| | | 428/156 |
| 2011/0149403 A1* | 6/2011 | Park ............... G02B 1/118 |
| | | 264/1.36 |
| 2011/0199561 A1* | 8/2011 | Hasegawa ............ G02B 5/30 |
| | | 349/96 |
| 2012/0127580 A1* | 5/2012 | Okamoto ............ G02B 1/118 |
| | | 359/601 |
| 2012/0134023 A1* | 5/2012 | Imaoku ............ G02F 1/133502 |
| | | 359/589 |
| 2012/0170126 A1* | 7/2012 | Imaoku ............ G02B 1/118 |
| | | 359/601 |
| 2013/0057958 A1* | 3/2013 | Minoura ............ C09J 133/10 |
| | | 359/601 |
| 2014/0049822 A1 | 2/2014 | Gollier |
| 2015/0177420 A1* | 6/2015 | Fujii ............... G02B 1/04 |
| | | 359/601 |
| 2015/0241603 A1 | 8/2015 | Fujii |
| 2016/0209995 A1* | 7/2016 | Jeon ............... G06T 5/003 |
| 2017/0102486 A1* | 4/2017 | Liu ............... G02F 1/133528 |
| 2018/0004333 A1 | 1/2018 | Jeong et al. |
| 2020/0241172 A1* | 7/2020 | Hayashi ............ G02B 1/116 |
| 2020/0363571 A1* | 11/2020 | Isshiki ............ G02B 1/115 |

FOREIGN PATENT DOCUMENTS

| | | |
|---|---|---|
| JP | 2012073487 A | 4/2012 |
| JP | 2013-78512 A | 5/2013 |
| JP | 2015-534096 A | 11/2015 |
| JP | 2016-197174 A | 11/2016 |
| JP | 2020-93956 A | 6/2020 |
| KR | 20060097608 A | 9/2006 |
| WO | 2009/144970 A1 | 12/2009 |
| WO | 2011/016270 A1 | 2/2011 |
| WO | 2011/067993 A1 | 6/2011 |
| WO | 2013/191092 A1 | 12/2013 |

\* cited by examiner

MEDICAL OBSERVATION SYSTEM AND DISPLAY DEVICE

CROSS-REFERENCE TO RELATED APPLICATIONS

The present application is based on PCT filing PCT/JP2020/027790, filed Jul. 17, 2020, which claims priority to JP 2019-140678, filed Jul. 31, 2019, the entire contents of each are incorporated herein by reference.

TECHNICAL FIELD

The present technology relates to a medical observation system and a display device, and particularly relates to a medical observation system and a display device capable of suppressing a decrease in bright place contrast and at the same time suppressing reflection of an image due to external light in display of a biological image related to a living body, for example.

BACKGROUND ART

For example, in Patent Documents 1 and 2, a display device including a display unit that displays an image and a transparent protective plate disposed on a front surface of the display unit is described.

In the display device described in Patent Document 1, a gap is provided between the display unit and the protective plate, and an air interface exists. Therefore, reflectance with respect to external light incident on the display device is high, a contrast (ratio) decreases in a bright place (bright) environment, and visibility decreases. Moreover, in the display device of Patent Document 1, dew condensation is likely to occur in the gap between the display unit and the protective plate in a high-temperature and high-humidity environment, a cold district, and the like, and visual recognition of an image displayed on the display unit may be hindered.

In the display device described in Patent Document 2, a space between the display unit and the protective plate is filled with an optical elastic resin or a transparent impact absorbing layer. Therefore, in the display device described in Patent Document 2, since there is no air interface, reflectance with respect to external light incident on the display device is reduced, and reflection of external light is suppressed. Moreover, in the display device described in Patent Document 2, dew condensation does not occur between the display unit and the protective plate, which occurs in the display device described in Patent Document 1, and an anti-fog property is high.

However, in the display device described in Patent Document 2, the space between the display unit and the protective plate is filled with the optical elastic resin and the like, and the display unit and the protective plate are integrally formed. Therefore, in a case where a defect such as a scratch, a crack, and the like occurs in the protective plate, it is difficult to replace only the protective plate. Therefore, even in a case where a defect occurs only in the protective plate, it is necessary to replace the display device, and replacement cost becomes expensive.

CITATION LIST

Patent Document

Patent Document 1: Japanese Patent Application Laid-Open No. 2016-197174

Patent Document 2: Japanese Patent Application Laid-Open No. 2013-078512

SUMMARY OF THE INVENTION

Problems to be Solved by the Invention

Incidentally, a medical display device used for medical treatment is often used in a bright place environment such as an operating room and the like, and reflection of an image due to specular reflection (mirror reflection) of external light incident on the display device hinders surgery and other medical practices. As a method of suppressing specular reflection of external light, there is a method of performing anti-glare (AG) processing such as attaching an AG film having an AG function and the like to a display screen of a display device to obscure an image reflected by the external light.

However, if the AG processing is performed on the display device, reflectance of the display screen increases, and the display screen appears whitish. Therefore, bright place contrast decreases as a result.

For a medical display device that displays a biological image related to a living body (patient and the like) of a medical treatment target, it is required to suppress a decrease in bright place contrast and at the same time reduce reflectance to suppress reflection of an image due to external light.

The present technology has been made in view of such a situation, and can suppress a decrease in bright place contrast and at the same time suppress reflection of an image due to external light in display of a biological image regarding a living body.

Solutions to Problems

A medical observation system of the present technology is a medical observation system including: an observation device that observes a living body of a medical treatment target; a signal processing device that generates a biological image related to the living body by processing an output signal of the observation device; and a display device including a display unit that displays the biological image and a transparent protective plate disposed on a front surface of the display unit, in which an uneven structure having unevenness with a pitch and a height smaller than a wavelength of visible light is formed on any one or more of a front surface side of the protective plate, a back surface side of the protective plate, and a front surface side of the display unit, and an anti-glare (AG) structure having an AG function is formed on any one or more of the front surface side of the protective plate, the back surface side of the protective plate, and the front surface side of the display unit.

A display device of the present technology is a display device including: a display unit that displays a biological image related to a living body of a medical treatment target; and a transparent protective plate disposed on a front surface of the display unit, in which an uneven structure having unevenness with a pitch and a height smaller than a wavelength of visible light is formed on any one or more of a front surface side of the protective plate, a back surface side of the protective plate, and a front surface side of the display unit, and an anti-glare (AG) structure having an AG function is formed on any one or more of the front surface side of the protective plate, the back surface side of the protective plate, and the front surface side of the display unit.

In a medical observation system and a display device of the present technology, a transparent protective plate is disposed on a front surface of a display unit that displays a biological image related to a living body of a medical treatment target. Then, an uneven structure having unevenness with a pitch and a height smaller than a wavelength of visible light is formed on any one or more of a front surface side of the protective plate, a back surface side of the protective plate, and a front surface side of the display unit, and an anti-glare (AG) structure having an AG function is formed on any one or more of the front surface side of the protective plate, the back surface side of the protective plate, and the front surface side of the display unit.

MODE FOR CARRYING OUT THE INVENTION

<Medical Observation System to which Present Technology is Applied>

Figure 1:
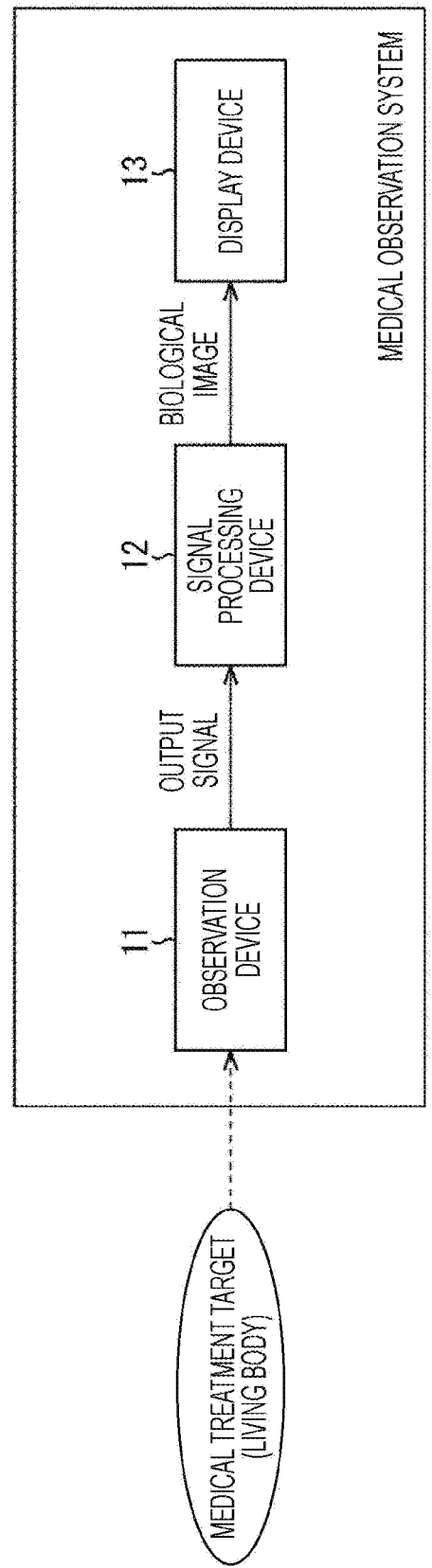
FIG. 1 is a block diagram illustrating a configuration example of an embodiment of a medical observation system to which the present technology is applied.

FIG. 1 is a block diagram showing a configuration example of an embodiment of a medical observation system to which the present technology is applied.

The medical observation system is a system for observing a living body of a medical treatment target, and is, for example, a medical endoscope system, a microscope system, an ultrasonic diagnosis system, and the like.

In FIG. 1, the medical observation system includes an observation device 11, a signal processing device 12, and a display device 13.

The observation device 11 observes a living body of a medical treatment target and outputs an output signal as an electric signal obtained by the observation. That is, the observation device 11 observes a living body by sensing light or a sound wave as a medium, and outputs an electric signal obtained by the sensing as an output signal. The observation device 11 is, for example, an endoscope (scope and camera head) of an endoscope system, a microscope of a microscope system, an ultrasonic probe of an ultrasonic diagnosis system, and the like.

The signal processing device 12 processes an output signal from the observation device 11 to generate a biological image regarding the living body observed by the observation device 11, and supplies the biological image to the display device 13. The signal processing device 12 is, for example, a camera control unit (CCU) of an endoscope system and a microscope system, a processing block of an ultrasonic diagnosis system that generates an image of a B mode and the like from a reflected wave of an ultrasonic wave, and the like.

The display device 13 displays a biological image from the signal processing device 12. That is, the display device 13 displays, for example, a biological image observed (imaged) with an endoscope or a microscope, or a biological image observed using an ultrasonic wave.

<Configuration Example of Display Device 13>

Figure 2:
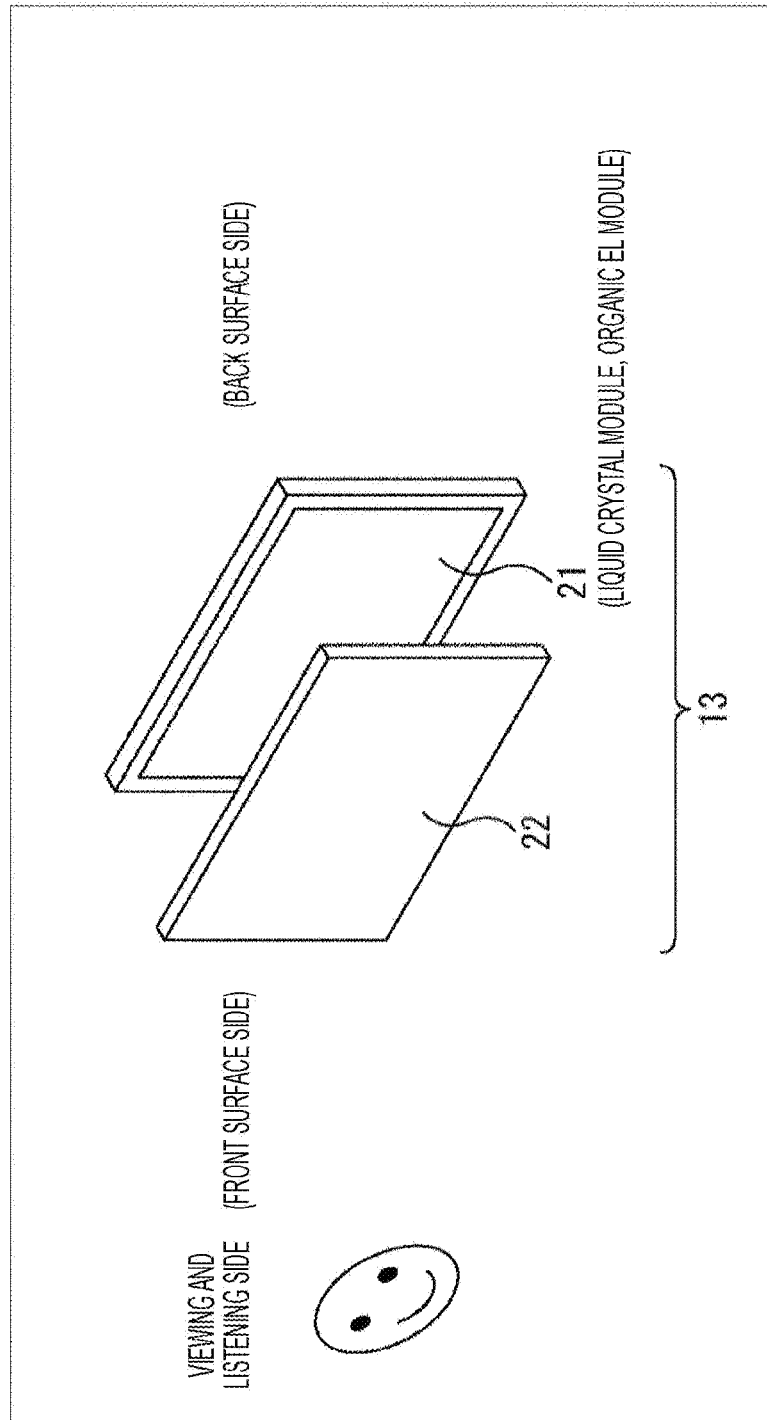
FIG. 2 is a perspective view illustrating a schematic configuration example of a display device 13.

FIG. 2 is a perspective view illustrating a schematic configuration example of the display device 13.

The display device 13 includes a display unit 21 and a protective plate 22.

The display unit 21 displays a biological image from the signal processing device 12 (FIG. 1). As the display unit 21, a liquid crystal module (panel), an organic electro luminescence (EL) module, and the like can be adopted.

The protective plate 22 is a flat plate including a transparent material, is disposed on a front surface side of the display unit 21, and protects a screen of the display unit 21.

Here, the front surface side is a side of the display unit 21 on which an image is displayed, that is, a user side in a case where a user views the image displayed on the display unit 21. The side opposite to the front surface side is referred to as a back surface side.

The protective plate 22 can include, for example, a resin such as acryl, polycarbonate, and the like, or glass such as chemically strengthened glass and the like as a base material. Since the protective plate 22 includes chemically strengthened glass, impact resistance of the protective plate 22 can be improved.

The display device 13 used in the medical observation system often receives a physical impact. For example, in a case where the medical observation system is an endoscope system, the display device 13 is mounted on a cart and moved for carrying in or out of an operating room and the like. In such movement in the cart, the display device 13 may receive a physical impact.

Furthermore, the display device 13 may be fixed to an arm fixed to a ceiling of the operating room. In this case, the display device 13 fixed to the arm may be moved according to a standing position of a medical professional, and the display device 13 may receive a physical impact during the movement.

As described above, the display device 13 used in the medical observation system has a much higher frequency of movement and a higher frequency of physical impact in the movement than a television receiver (TV) fixed to a wall or placed on a television stand, or a personal computer (PC) monitor placed on a desk. Therefore, the protective plate 22 of the display device 13 is required to have impact resistance. Since the protective plate 22 includes chemically strengthened glass, impact resistance of the protective plate 22 can be improved.

Figure 3:
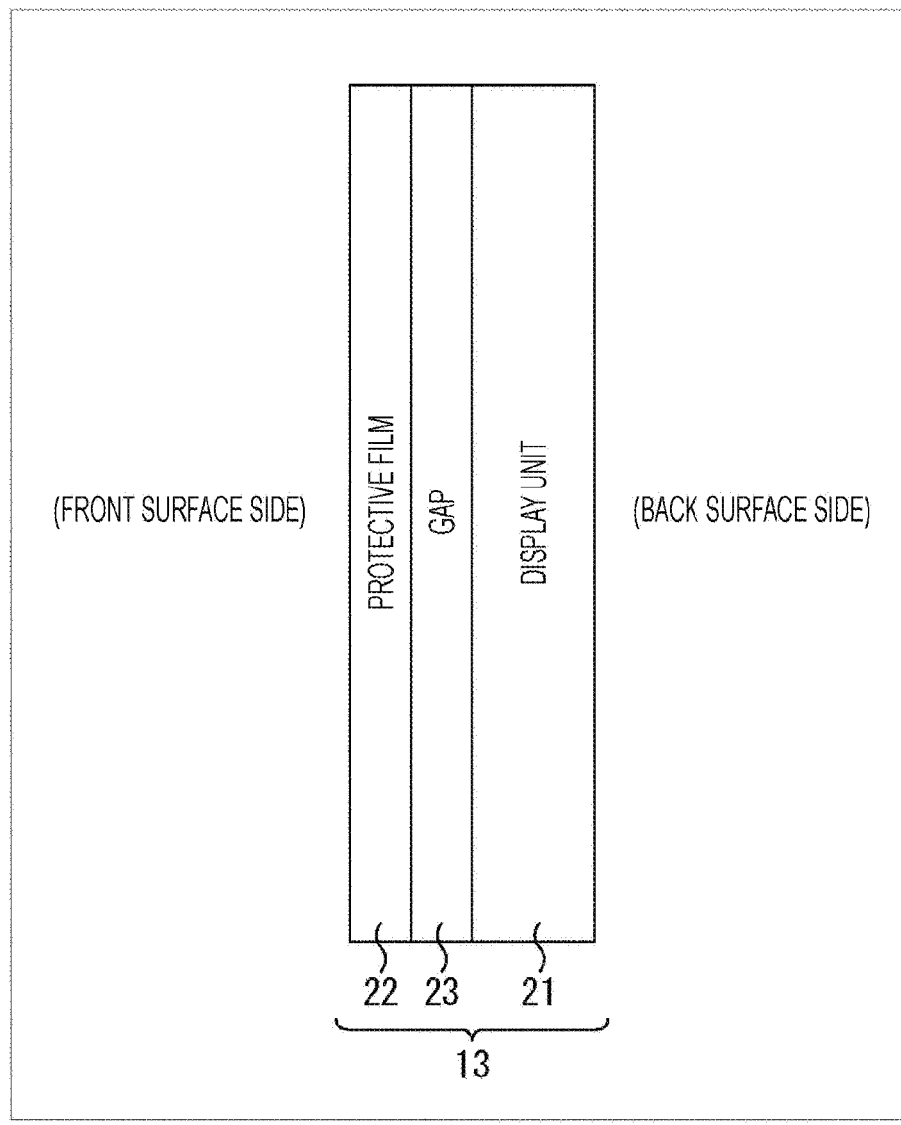
FIG. 3 is a sectional view illustrating a schematic configuration example of the display device 13.

FIG. 3 is a sectional view illustrating a schematic configuration example of the display device 13.

In the display device 13, the protective plate 22 is fixed to a front surface of the display unit 21 such that a gap 23 is formed between the display unit 21 and the protective plate 22.

In the display device 13, unlike the display device described in Patent Document 2, the gap 23 is formed between the display unit 21 and the protective plate 22 instead of filling a space between the display unit 21 and the protective plate 22 with an optical elastic resin and the like. Therefore, due to a structure in which the gap 23 is formed, only the protective plate 22 can be easily removed from the display device 13 as compared with a case where the space between the display unit 21 and the protective plate 22 is filled with the optical elastic resin and the like. As a result, the protective plate 22 can be easily repaired, reworked, and replaced.

As described with reference to FIG. 2, since the display device 13 is frequently subjected to a physical impact, defects such as a scratch, a crack, and the like are likely to occur in the protective plate 22 of the display device 13. Then, in a case where a defect occurs only in the protective plate 22, repair cost increases by replacing the whole display device 13. As for the display device 13, in a case where the defect occurs only in the protective plate 22, only the protective plate 22 can be easily replaced. Therefore, it is possible to apply a service of replacing only the protective plate 22 (to facilitate maintenance and improve serviceability), and it is possible to suppress repair cost in a case where the defect occurs only in the protective plate 22.

Figure 4:
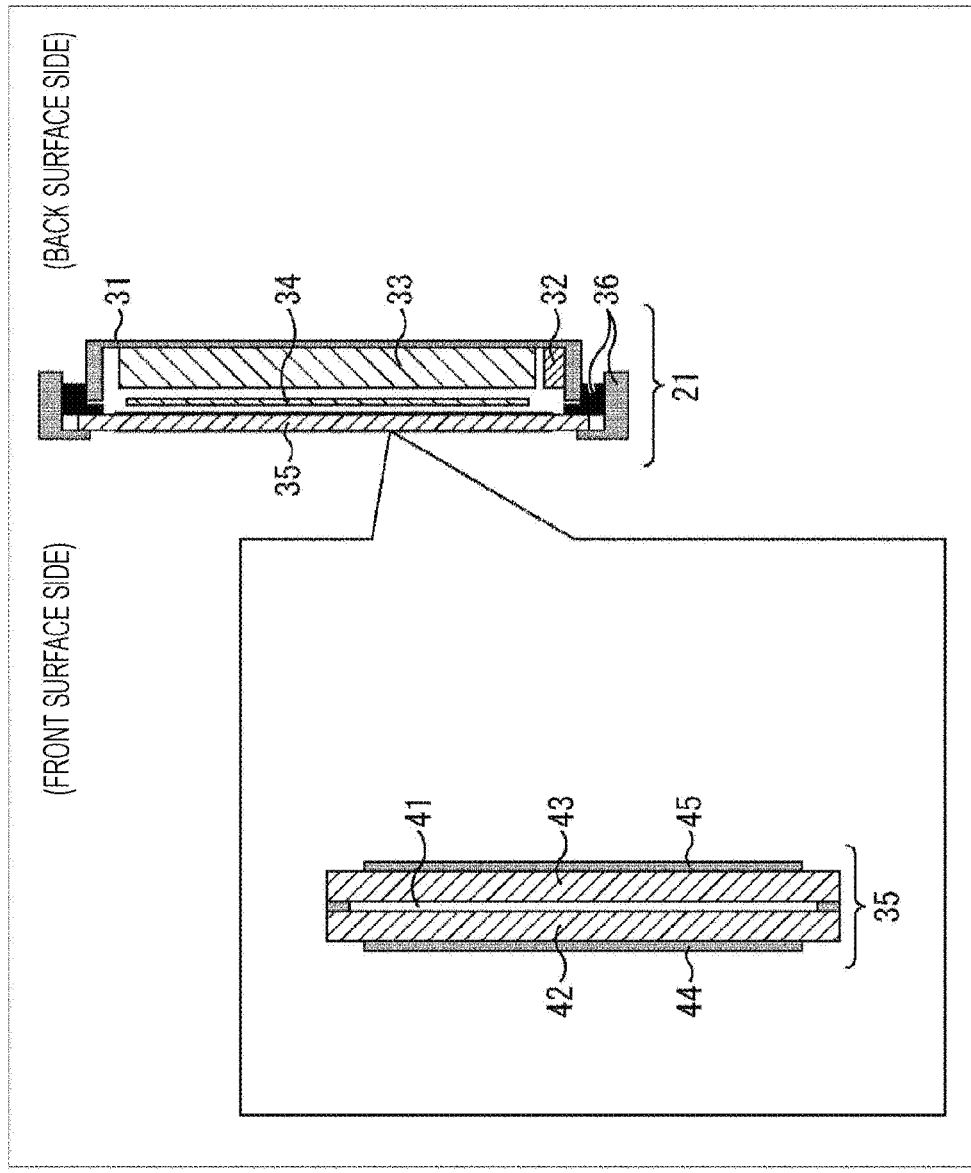
FIG. 4 is a sectional view illustrating a first configuration example of a display unit 21.

FIG. 4 is a sectional view illustrating a first configuration example of the display unit 21.

FIG. 4 illustrates a configuration example of the display unit 21 in a case where the display unit 21 is a liquid crystal module (panel).

In FIG. 4, a light source 32, a light guide plate 33, and an optical sheet 34 are housed in a housing 31 on a back surface side of the display unit 21. A liquid crystal element (cell) 35 is provided on a front surface side of the optical sheet 34. The liquid crystal element 35 is supported by a bezel 36 fixed to the housing 31, and therefore, is fixed to the front surface side of the optical sheet 34.

In the liquid crystal element 35, a liquid crystal 41 is sandwiched between a glass 42 on the front surface side and a glass 43 on the back surface side. Then, a polarizing plate 44 is bonded to a front surface side of the glass 42, and a polarizing plate 45 is bonded to a back surface side of the glass 43.

In the display unit 21 configured as described above, the back surface side of the liquid crystal element 35 is irradiated with light emitted from the light source 32 via the light guide plate 33 and the optical sheet 34.

In the liquid crystal element 35, transmission of the light with which the back surface side is irradiated is controlled by the liquid crystal 41 sandwiched between the glasses 42 and 43 and the polarizing plates 44 and 45, whereby an image is displayed.

Figure 5:
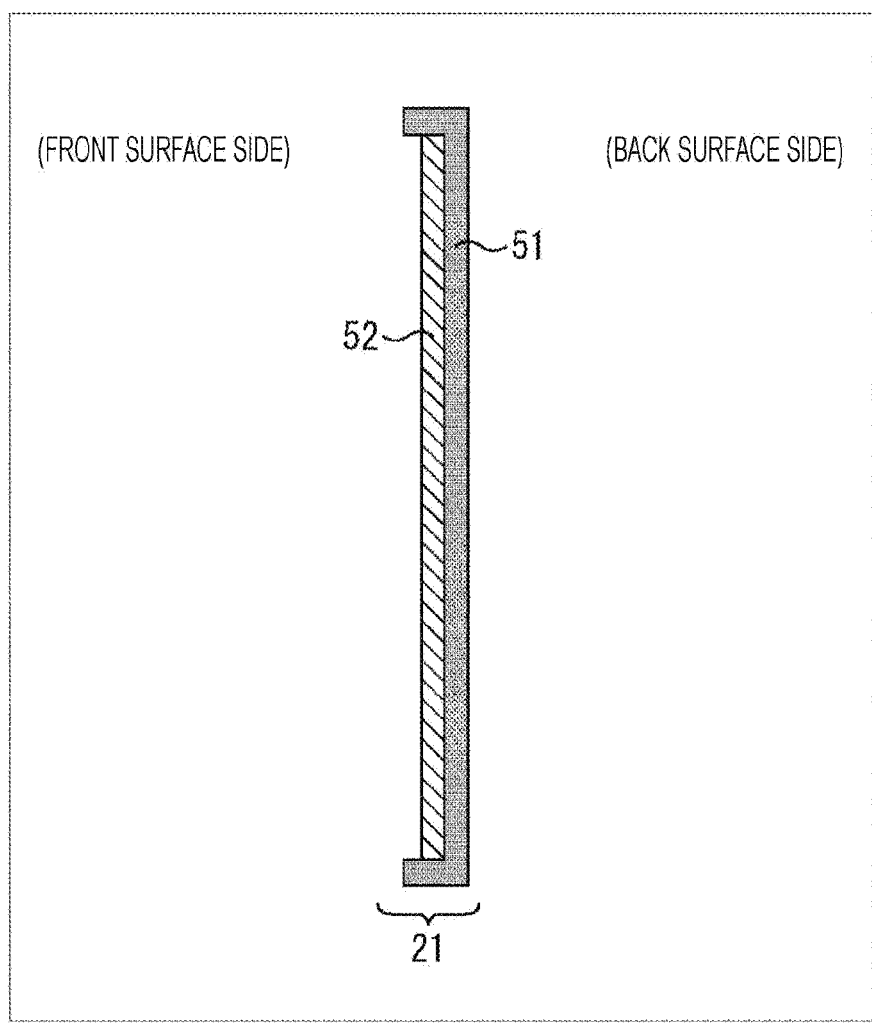
FIG. 5 is a sectional view illustrating a second configuration example of the display unit 21.

FIG. 5 is a sectional view illustrating a second configuration example of the display unit 21.

FIG. 5 illustrates a configuration example of the display unit 21 in a case where the display unit 21 is an organic EL module (panel).

In FIG. 5, an organic EL element 52 is housed in a housing 51 on the back surface side of the display unit 21.

In the display unit 21 configured as described above, the organic EL element 52 housed in the housing 51 emits light to display an image.

Hereinafter, a detailed configuration example of the display device 13 will be described assuming that the display unit 21 is a liquid crystal module as illustrated in FIG. 4.

Figure 6:
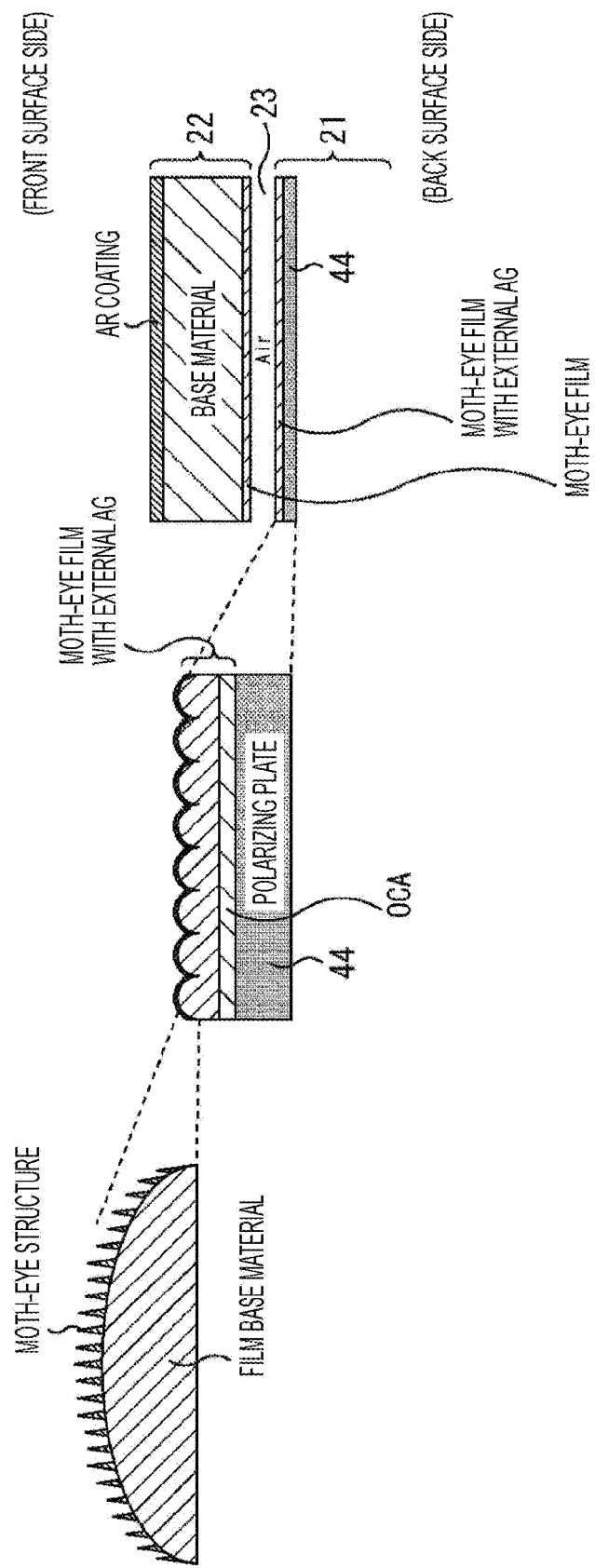
FIG. 6 is a sectional view illustrating a first detailed configuration example of the display device 13.

FIG. 6 is a sectional view illustrating a first detailed configuration example of the display device 13.

Note that, in FIG. 6, an upper side in the drawing is a front surface side of the display device 13, and a lower side is a back surface side of the display device 13. The same applies to subsequent sectional views.

In the display device 13, an AG structure having an AG function is formed on any one or more of a front surface side of the protective plate 22, a back surface side of the protective plate 22, and a front surface side of the display unit 21.

Moreover, in the display device 13, an anti-reflection (AR) structure having an AR function is formed on any one or more of the front surface side of the protective plate 22, the back surface side of the protective plate 22, and the front surface side of the display unit 21.

As described above, since each of the AG structure and the AR structure is formed on any one or more of the front surface side of the protective plate 22, the back surface side of the protective plate 22, and the front surface side of the display unit 21, it is possible to simultaneously realize suppression of reflection of an image due to external light by the AG structure and low reflectance by the AR structure in display of a biological image on the display device 13. As a result, it is possible to suppress a decrease in bright place contrast and at the same time suppress reflection of an image due to external light.

Here, dark place contrast is a ratio of white luminance and black luminance, and the bright place contrast is a ratio of white luminance and a sum of black luminance and luminance corresponding to reflection of external light. Therefore, the bright place contrast deteriorates (decreases) if reflectance with respect to external light is high. According to the display device 13, since the low reflectance by the AR structure is realized, it is possible to suppress a decrease in the bright place contrast. As a result, a dynamic range of the display device 13 (a difference between the brightest portion and the darkest portion of a biological image displayed on the display device 13) can be improved. Therefore, it is possible to improve visibility of the biological image in a bright place environment such as a medical site.

Furthermore, in the display device 13, reflection of light as a biological image displayed by the display unit 21 at an interface of the protective plate 22 and the like is suppressed by the AR structure, and luminance of the biological image can be improved by, for example, about 2 to 4%.

In the display device 13, the gap 23 can be formed without the need for filling the space between the display unit 21 and the protective plate 22 with an optical elastic resin and the like as in Patent Document 2, in order to realize low reflection. Therefore, in the display device 13, the display unit 21 and the protective plate 22 are not integrated, and only the protective plate 22 can be easily replaced.

As specific examples of the AG structure, for example, there are (a layer of) an optical clear adhesive (OCA) containing a diffusion material obtained by mixing a filler as the diffusion material with the OCA as an adhesive for bonding components, an uneven structure (another uneven structure) having unevenness with a pitch (sufficiently) larger than a wavelength of visible light and smaller than a pixel pitch of the display unit 21, and the like.

As a method of forming the AG structure in the display device 13, there are a method of using the OCA containing the diffusion material for bonding components, a method of forming a surface of the component into an uneven structure as the AG structure, a method of bonding (attaching) a film having an uneven structure as the AG structure, and the like.

As specific examples of the AR structure, for example, there are a thin film (structure) that reduces reflected light using light interference, a moth-eye structure, and the like.

The moth-eye structure is an uneven structure having a fine uneven shape and having unevenness with a pitch and a height smaller than a wavelength of visible light, and reflection of visible light is prevented (suppressed) by providing the moth-eye structure at an interface between substances having different refractive indexes. According to the moth-eye structure, space occupancy of both the substances forming the interface in a height direction of the fine unevenness gradually changes, and a substance having larger space occupancy is replaced with a change in position of the fine unevenness in the height direction, so that the refractive index also smoothly changes. As the refractive index gradually changes in this manner, reflection of visible light is suppressed.

Note that the moth-eye structure can be said to have a recessed shape with reference to the uppermost portion of a projection of the unevenness, and can be said to have a projecting shape with reference to the lowermost portion of a recess of the unevenness. The recess and the projection of the moth-eye structure preferably have a substantially conical shape or a substantially pyramidal shape, but may have a substantially columnar shape or a substantially prismatic shape.

As a method of forming the AR structure, for example, there are a method of forming a thin film as the AR structure by coating and a method of bonding a thin film as the AR structure. Moreover, for example, there are a method of forming a moth-eye structure as the AR structure on a surface of a component, a method of bonding a film having a moth-eye structure (hereinafter, also referred to as a moth-eye film) as the AR structure, and the like.

In FIG. 6, a moth-eye film with external AG is bonded to a front surface of the polarizing plate 44 of the display unit 21 with an OCA.

The moth-eye film with the external AG is a (an optical) film in which an uneven structure (uneven structure with a pitch larger than a wavelength of visible light and smaller than a pixel pitch of the display unit 21) as an AG structure is formed on a film base material, and moreover, a moth-eye structure is formed on the uneven structure as the AG structure. In FIG. 6, the uneven structure as the AG structure has spherical unevenness, but a shape of the uneven structure as the AG structure is not limited to the spherical shape.

In the moth-eye film with the external AG, in addition to forming the uneven structure as the AG structure on the film base material, the film base material itself can be formed into an uneven structure as an AG structure, and a moth-eye structure can be formed on the uneven structure as the AG structure.

According to the moth-eye film with the external AG, the uneven structure as the AG structure exerts an AG function by diffusing reflected light of external light, and the moth-eye structure exerts an AR function by changing a refractive index of the interface.

It can be said that both the AG structure and the AR structure are formed on (the polarizing plate 44 on) the front surface of the display unit 21 to which the moth-eye film with the external AG is bonded.

In FIG. 6, a moth-eye film is bonded to a back surface of (the base material constituting) the protective plate 22 with the OCA, and a thin film as an AR structure is coated on a front surface of the protective plate 22. Here, the coated thin film as the AR structure is also referred to as an AR coating.

It can be said that the AR structure is formed on the back surface of the protective plate 22 to which the moth-eye film is bonded. It can be said that the AG structure is formed on the front surface of the protective plate 22 on which the AR coating is formed.

In FIG. 6, an AR film that exhibits the AR function can be bonded to the front surface of the protective plate 22 instead of forming the AR coating.

However, while the AR film has surface hardness of about 3 H, the AR coating can achieve surface hardness of 6 H or more. Therefore, by making the front surface of the protective plate 22 film-less and forming the AR coating, resistance to damage such as a scratch and the like occurring in the protective plate 22 can be improved.

Note that, if the AG structure is arranged at a position far from pixels of the display unit 21, boundaries of the pixels become unclear in the biological image displayed on the display device 13, and definition (resolution) of the biological image decreases. In recent years, definition of the pixels of the display unit 21 has been increased, and it is necessary to suppress a decrease in definition of the biological image due to the arrangement of the AG structure. By arranging the AG structure at a position closer to the display unit 21, it is possible to suppress the decrease in definition of the biological image.

Furthermore, in the uneven structure as the AG structure, glare (luminance unevenness) can occur by a lens effect due to the unevenness, but this glare can be prevented by making a pitch of the unevenness of the uneven structure as the AG structure sufficiently smaller than the pixel pitch.

The moth-eye film and the moth-eye film with the external AG can include a hydrophilic or hydrophobic material.

In a case where the moth-eye film and the moth-eye film with the external AG include the hydrophilic material, a surface area where moisture comes into contact with the moth-eye structure becomes large, so that a contact angle of moisture adhering to the moth-eye structure decreases, and the moisture is thinned without forming water droplets. Therefore, even if dew condensation occurs, the dew condensation cannot be visually recognized.

In a case where the moth-eye film and the moth-eye film with the external AG include the hydrophobic material, the contact angle of moisture adhering to the moth-eye structure increases. The moisture becomes water droplets, and they fall by their own weight.

Here, the display device 13 used for medical treatment may be stored without being controlled in temperature and humidity. In this case, in a high-temperature and high-humidity region, a cold district, and the like, if highly humid air enters the gap 23 between the display unit 21 and the protective plate 22 and the surface is cooled, dew condensation may occur, and the inside of the gap 23 may be fogged.

If the inside of the gap 23 is fogged, the biological image displayed on the display unit 21 becomes difficult to be visually recognized, and treatment while viewing the biological image is hindered, which is likely to lead to erroneous treatment.

By making the moth-eye film and the moth-eye film with the external AG of the hydrophilic or hydrophobic material, it is possible to prevent the inside of the gap 23 from being fogged and to improve an anti-fog property.

Figure 7:
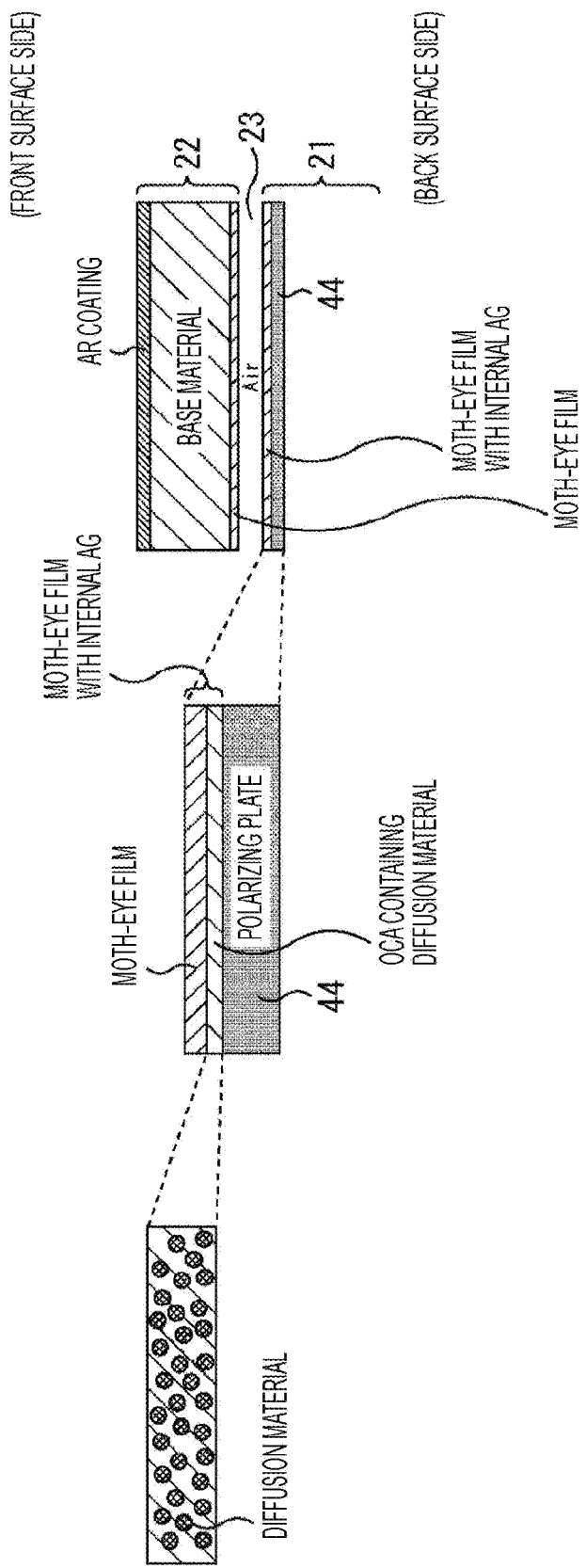
FIG. 7 is a sectional view illustrating a second detailed configuration example of the display device 13.

FIG. 7 is a sectional view illustrating a second detailed configuration example of the display device 13.

In FIG. 7, a moth-eye film with internal AG is bonded to the front surface of the polarizing plate 44 of the display unit 21.

The moth-eye film with the internal AG is a moth-eye film bonded with an OCA containing a diffusion material in which a diffusion material having a size smaller than the pixel pitch of the display unit 21 is mixed with the OCA. By adopting the diffusion material having the size smaller than the pixel pitch, glare caused by the lens effect described in FIG. 6 can be prevented.

In the moth-eye film with the internal AG, (a layer of) the OCA containing the diffusion material that bonds the moth-eye film to (the polarizing plate 44 of) the front surface of the display unit 21 constitutes an AG structure.

According to the moth-eye film with the internal AG, the OCA containing the diffusion material as the AG structure diffuses reflected light of external light to exhibit an AG function, and a moth-eye structure of the moth-eye film changes a refractive index of the interface to exhibit an AR function.

It can be said that both the AG structure and the AR structure are formed on (the polarizing plate 44 of) the front surface of the display unit 21 to which the moth-eye film with the internal AG is bonded.

In FIG. 7, similarly to FIG. 6, a moth-eye film is bonded to the back surface of the protective plate 22 with an OCA, and an AR coating is formed on the front surface of the protective plate 22.

Figure 8:
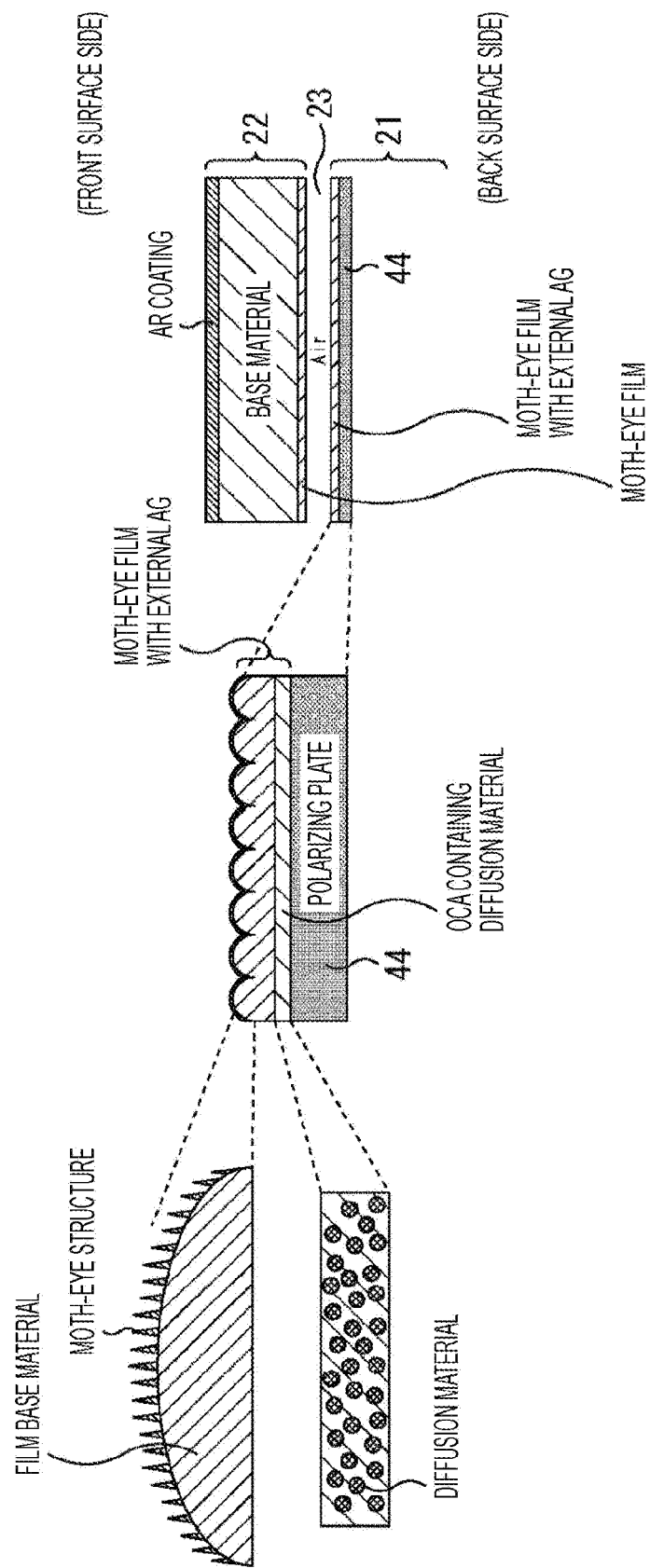
FIG. 8 is a sectional view illustrating a third detailed configuration example of the display device 13.

FIG. 8 is a sectional view illustrating a third detailed configuration example of the display device 13.

The display device 13 of FIG. 8 is configured similarly to the case of FIG. 6 except that the moth-eye film with the external AG is not bonded to the front surface of the display unit 21 with a (simple) OCA but bonded to the front surface of the display unit 21 with an OCA containing a diffusion material.

In FIG. 8, an uneven structure (uneven structure as the AG structure) having a pitch larger than a wavelength of visible light and smaller than a pixel pitch of the moth-eye film with the external AG and the OCA containing the diffusion material are provided as an AG structure. Since the OCA containing the diffusion material exists at a position closer to the display unit 21 than the uneven structure as the AG structure, in the display device 13 of FIG. 8 in which the OCA containing the diffusion material is used, it is possible to further suppress a decrease in definition of a biological image as compared with the display device 13 of FIG. 6 in which the OCA containing the diffusion material is not used. The same applies to the display device 13 in FIG. 7.

Figure 9:
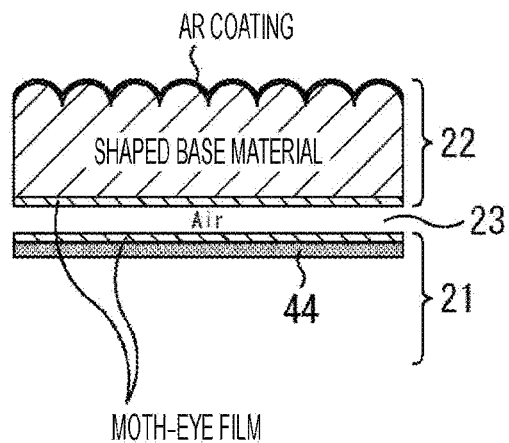
FIG. 9 is a sectional view illustrating a fourth detailed configuration example of the display device 13.

FIG. 9 is a sectional view illustrating a fourth detailed configuration example of the display device 13.

In FIG. 9, a moth-eye film as an AR structure is bonded to the front surface of the polarizing plate 44 of the display unit 21 and the back surface of the protective plate 22 with an OCA.

Moreover, the front surface of the protective plate 22 has an uneven structure having an AG structure, that is, an uneven structure having a pitch larger than a wavelength of visible light and smaller than a pixel pitch.

Note that, regarding the protective plate 22, only the front surface can have the uneven structure having the AG structure, and in addition, only the back surface or both the front surface and the back surface can have the uneven structure having the AG structure.

In FIG. 9, by shaping one surface of flat glass, resin, and the like into the uneven structure having the AG structure, the protective plate 22 becomes, for example, a ground glass protective plate in which the front surface has the uneven structure having the AG structure. Then, an AR coating is formed on the uneven structure having the AG structure on the front surface of such a protective plate 22.

Figure 10:
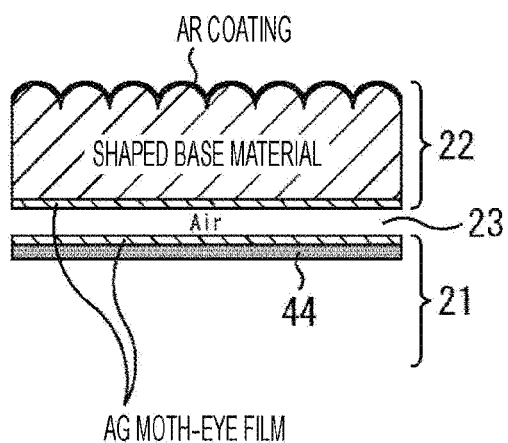
FIG. 10 is a sectional view illustrating a fifth detailed configuration example of the display device 13.

FIG. 10 is a sectional view illustrating a fifth detailed configuration example of the display device 13.

In FIG. 10, an AG moth-eye film is bonded to the front surface of the polarizing plate 44 of the display unit 21 and the back surface of the protective plate 22.

Here, the AG moth-eye film means a moth-eye film with external AG, that is, a film in which a moth-eye structure is formed on an uneven structure as an AG structure, or a moth-eye film with internal AG, that is, a moth-eye film bonded with an OCA containing a diffusion material.

Moreover, in FIG. 10, similarly to FIG. 9, the front surface of the protective plate 22 has an uneven structure having an AG structure, and an AR coating is formed on the uneven structure having the AG structure.

Figure 11:
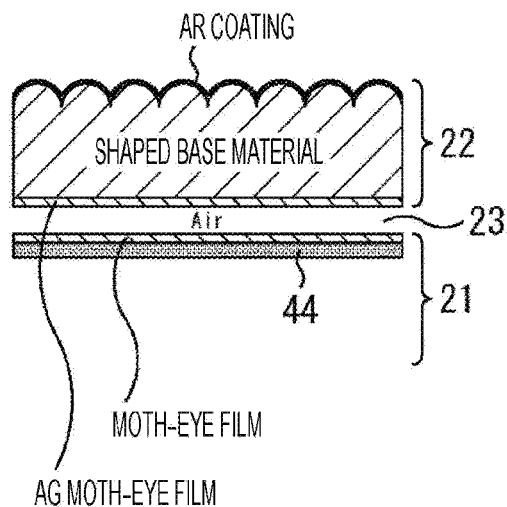
FIG. 11 is a sectional view illustrating a sixth detailed configuration example of the display device 13.

FIG. 11 is a sectional view illustrating a sixth detailed configuration example of the display device 13.

In FIG. 11, a moth-eye film is bonded to the front surface of the polarizing plate 44 of the display unit 21 with an OCA, and an AG moth-eye film is bonded to the back surface of the protective plate 22.

Moreover, in FIG. 11, similarly to FIG. 9, the front surface of the protective plate 22 has an uneven structure having an AG structure, and an AR coating is formed on the uneven structure having the AG structure.

Figure 12:
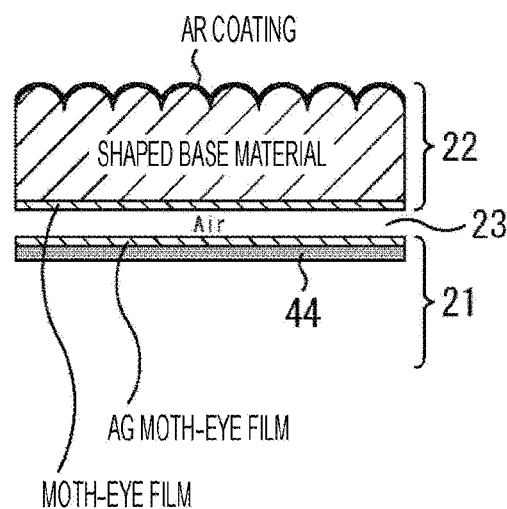
FIG. 12 is a sectional view illustrating a seventh detailed configuration example of the display device 13.

FIG. 12 is a sectional view illustrating a seventh detailed configuration example of the display device 13.

In FIG. 12, an AG moth-eye film is bonded to the front surface of the polarizing plate 44 of the display unit 21, and a moth-eye film is bonded to the back surface of the protective plate 22 with an OCA.

Moreover, in FIG. 12, similarly to FIG. 9, the front surface of the protective plate 22 has an uneven structure having an AG structure, and an AR coating is formed on the uneven structure having the AG structure.

Figure 13:
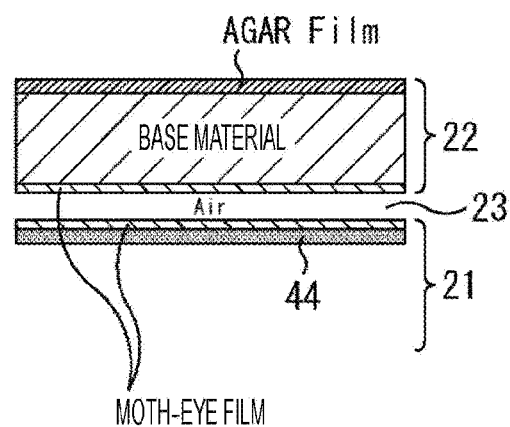
FIG. 13 is a sectional view illustrating an eighth detailed configuration example of the display device 13.

FIG. 13 is a sectional view illustrating an eighth detailed configuration example of the display device 13.

In FIG. 13, a moth-eye film is bonded to the front surface of the polarizing plate 44 of the display unit 21 and the back surface of the protective plate 22 with an OCA.

Moreover, in FIG. 13, an AGAR film is bonded to the front surface of the protective plate 22 with the OCA.

The AGAR film is, for example, a film having both an AG function by a laminated structure and an AR function by surface diffusion treatment. Therefore, in FIG. 13, it can be said that both an AG structure and an AR structure are formed on the front surface of the protective plate 22.

Figure 14:
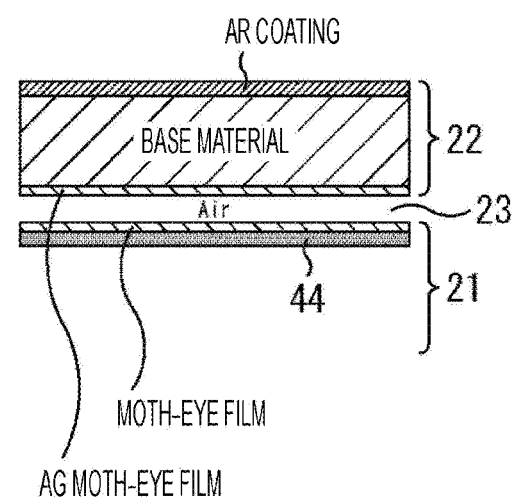
FIG. 14 is a sectional view illustrating a ninth detailed configuration example of the display device 13.

FIG. 14 is a sectional view illustrating a ninth detailed configuration example of the display device 13.

In FIG. 14, a moth-eye film is bonded to the front surface of the polarizing plate 44 of the display unit 21 with an OCA, and an AG moth-eye film is bonded to the back surface of the protective plate 22.

Moreover, in FIG. 14, an AR coating is formed on the front surface of the protective plate 22.

Figure 15:
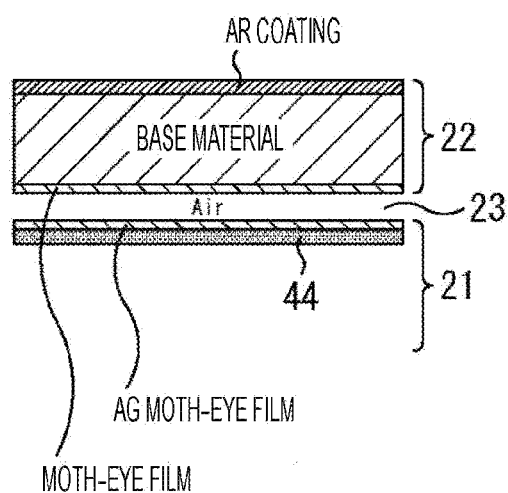
FIG. 15 is a sectional view illustrating a 10th detailed configuration example of the display device 13.

FIG. 15 is a sectional view illustrating a 10th detailed configuration example of the display device 13.

In FIG. 15, an AG moth-eye film is bonded to the front surface of the polarizing plate 44 of the display unit 21, and a moth-eye film is bonded to the back surface of the protective plate 22 with an OCA.

Moreover, in FIG. 15, an AR coating is formed on the front surface of the protective plate 22.

Figure 16:
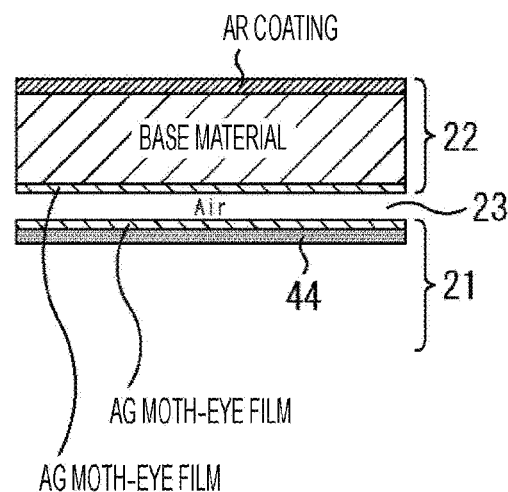
FIG. 16 is a sectional view illustrating an 11th detailed configuration example of the display device 13.

FIG. 16 is a sectional view illustrating an 11th detailed configuration example of the display device 13.

In FIG. 16, an AG moth-eye film is bonded to the front surface of the polarizing plate 44 of the display unit 21 and the back surface of the protective plate 22.

Moreover, in FIG. 16, an AR coating is formed on the front surface of the protective plate 22.

Figure 17:
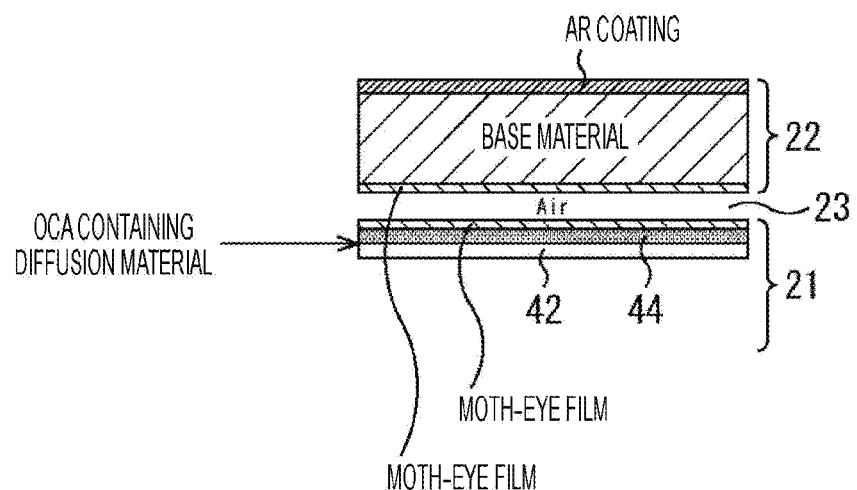
FIG. 17 is a sectional view illustrating a 12th detailed configuration example of the display device 13.

FIG. 17 is a sectional view illustrating a 12th detailed configuration example of the display device 13.

In FIG. 17, a moth-eye film is bonded to the front surface of the polarizing plate 44 of the display unit 21 and the back surface of the protective plate 22 with an OCA.

Moreover, in FIG. 17, an AR coating is formed on the front surface of the protective plate 22.

Then, in FIG. 17, an OCA containing a diffusion material having an AG structure is used as an adhesive for bonding the polarizing plate 44 and the glass 42 of the display unit 21 (FIG. 4).

Therefore, in FIG. 17, it can be said that an AR structure by the moth-eye film and the AG structure by (a layer of) the OCA containing the diffusion material are formed on the front surface of the display unit 21.

In FIGS. 7 and 8, the AG structure by the OCA containing the diffusion material is provided on the front surface of the polarizing plate 44, whereas in FIG. 17, the AG structure by the OCA containing the diffusion material is provided on the back surface of the polarizing plate 44. Therefore, in FIG. 17, since the AG structure by the OCA containing the diffusion material exists at a position closer to the display unit 21 than in the cases of FIGS. 7 and 8, it is possible to further suppress a decrease in definition of a biological image as compared with the cases of FIGS. 7 and 8.

Figure 18:
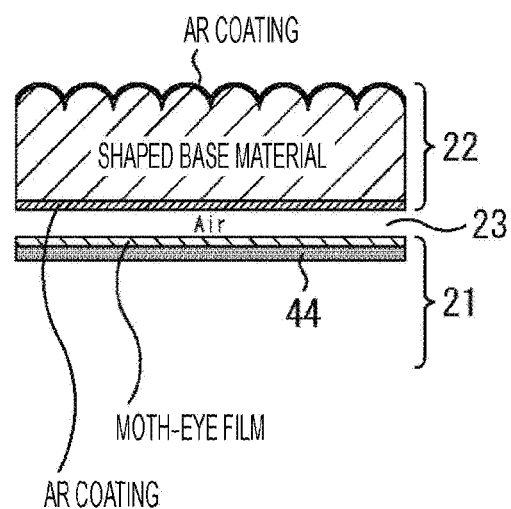
FIG. 18 is a sectional view illustrating a 13th detailed configuration example of the display device 13.

FIG. 18 is a sectional view illustrating a 13th detailed configuration example of the display device 13.

In FIG. 18, a moth-eye film is bonded to the front surface of the polarizing plate 44 of the display unit 21 with an OCA, and an AR coating is formed on the back surface of the protective plate 22.

Moreover, in FIG. 18, similarly to FIG. 9, the front surface of the protective plate 22 has an uneven structure having an AG structure, and the AR coating is formed on the uneven structure having the AG structure.

Figure 19:
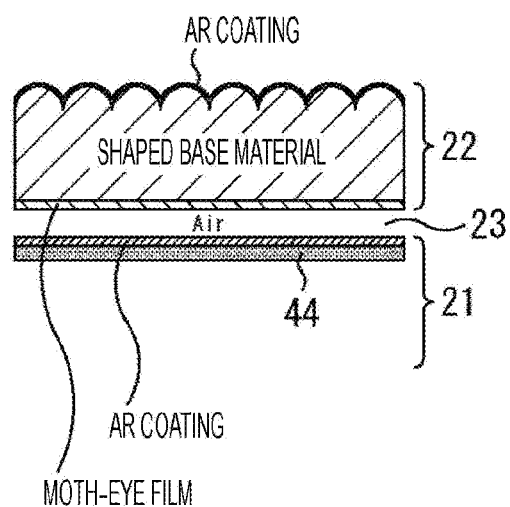
FIG. 19 is a sectional view illustrating a 14th detailed configuration example of the display device 13.

FIG. 19 is a sectional view illustrating a 14th detailed configuration example of the display device 13.

In FIG. 19, an AR coating is formed on the front surface of the polarizing plate 44 of the display unit 21, and a moth-eye film is bonded to the back surface of the protective plate 22 with an OCA.

Moreover, in FIG. 19, similarly to FIG. 9, the front surface of the protective plate 22 has an uneven structure having an AG structure, and the AR coating is formed on the uneven structure having the AG structure.

Figure 20:
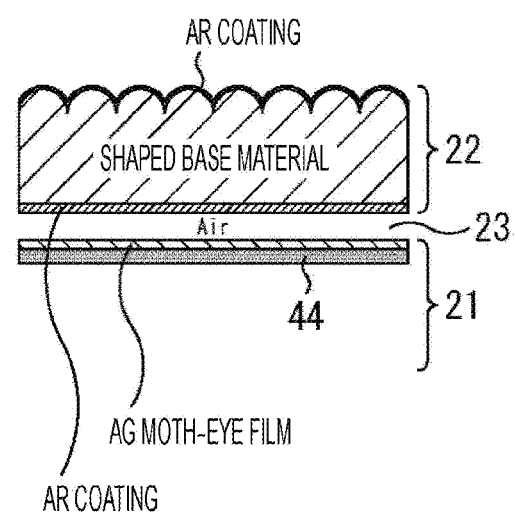
FIG. 20 is a sectional view illustrating a 15th detailed configuration example of the display device 13.

FIG. 20 is a sectional view illustrating a 15th detailed configuration example of the display device 13.

In FIG. 20, an AG moth-eye film is bonded to the front surface of the polarizing plate 44 of the display unit 21, and an AR coating is formed on the back surface of the protective plate 22.

Moreover, in FIG. 20, similarly to FIG. 9, the front surface of the protective plate 22 has an uneven structure having an AG structure, and the AR coating is formed on the uneven structure having the AG structure.

Figure 21:
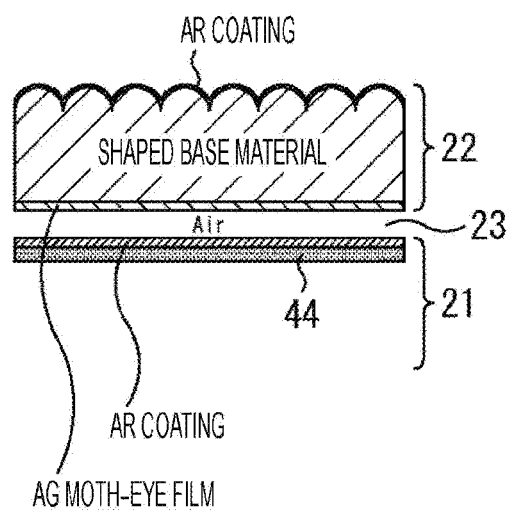
FIG. 21 is a sectional view illustrating a 16th detailed configuration example of the display device 13.

FIG. 21 is a sectional view illustrating a 16th detailed configuration example of the display device 13.

In FIG. 21, an AR coating is formed on the front surface of the polarizing plate 44 of the display unit 21, and an AG moth-eye film is bonded to the back surface of the protective plate 22.

Moreover, in FIG. 21, similarly to FIG. 9, the front surface of the protective plate 22 has an uneven structure having an AG structure, and the AR coating is formed on the uneven structure having the AG structure.

Figure 22:
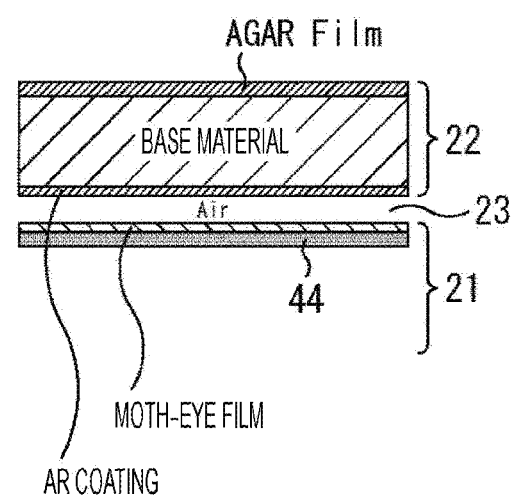
FIG. 22 is a sectional view illustrating a 17th detailed configuration example of the display device 13.

FIG. 22 is a sectional view illustrating a 17th detailed configuration example of the display device 13.

In FIG. 22, a moth-eye film is bonded to the front surface of the polarizing plate 44 of the display unit 21 with an OCA, and an AR coating is formed on the back surface of the protective plate 22.

Moreover, in FIG. 22, an AGAR film is bonded to the front surface of the protective plate 22 with the OCA.

Figure 23:
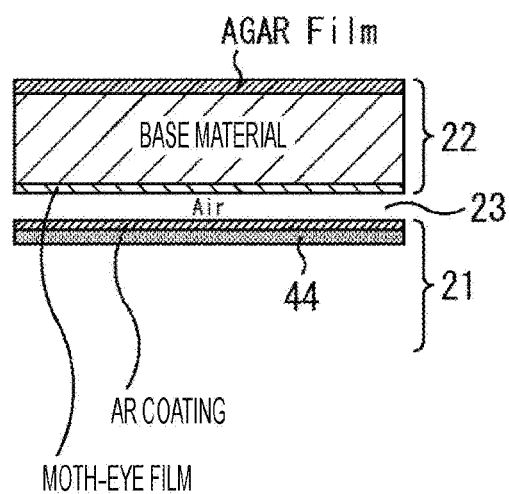
FIG. 23 is a sectional view illustrating an 18th detailed configuration example of the display device 13.

FIG. 23 is a sectional view illustrating an 18th detailed configuration example of the display device 13.

In FIG. 23, an AR coating is formed on the front surface of the polarizing plate 44 of the display unit 21, and a moth-eye film is bonded to the back surface of the protective plate 22 with an OCA.

Moreover, in FIG. 23, an AGAR film is bonded to the front surface of the protective plate 22 with the OCA.

Figure 24:
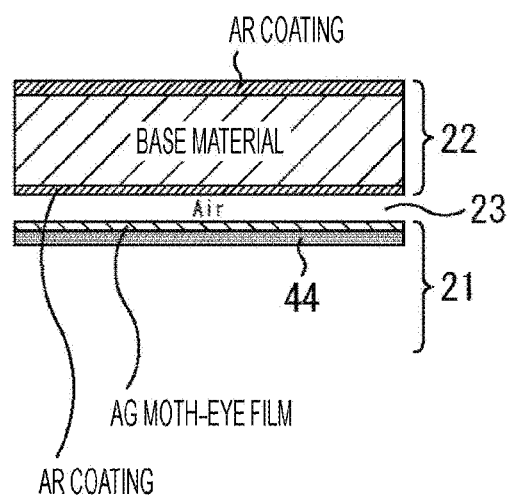
FIG. 24 is a sectional view illustrating a 19th detailed configuration example of the display device 13.

FIG. 24 is a sectional view illustrating a 19th detailed configuration example of the display device 13.

In FIG. 24, an AG moth-eye film is bonded to the front surface of the polarizing plate 44 of the display unit 21, and an AR coating is formed on the back surface and the front surface of the protective plate 22.

Figure 25:
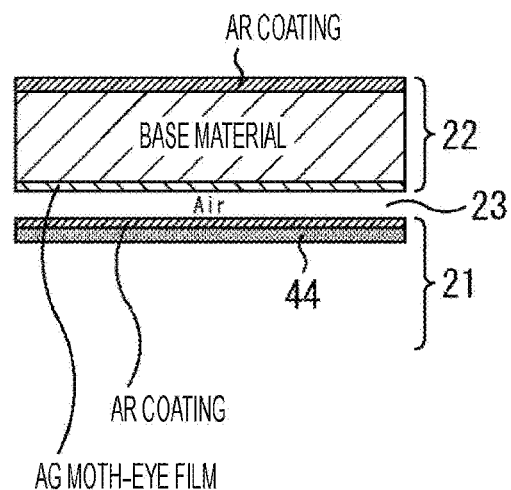
FIG. 25 is a sectional view illustrating a 20th detailed configuration example of the display device 13.

FIG. 25 is a sectional view illustrating a 20th detailed configuration example of the display device 13.

In FIG. 25, an AR coating is formed on the front surface of the polarizing plate 44 of the display unit 21, and an AG moth-eye film is bonded to the back surface of the protective plate 22.

Moreover, in FIG. 25, the AR coating is formed on the front surface of the protective plate 22.

Figure 26:
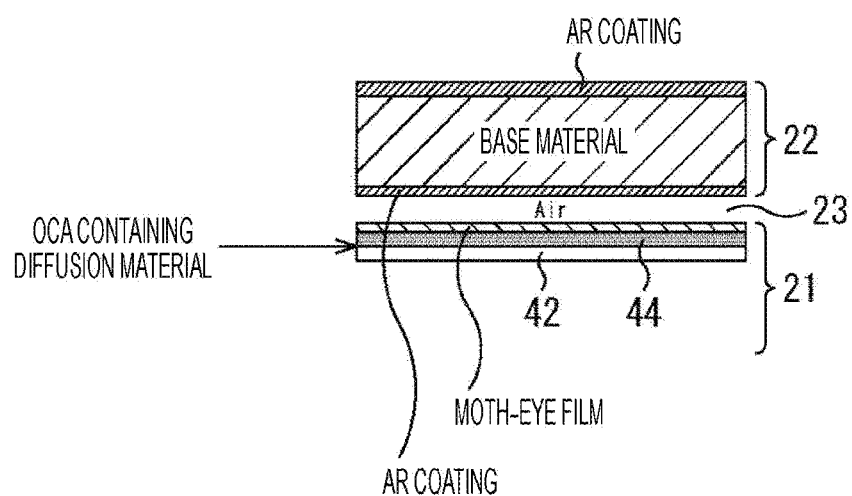
FIG. 26 is a sectional view illustrating a 21st detailed configuration example of the display device 13.

FIG. 26 is a sectional view illustrating a 21st detailed configuration example of the display device 13.

In FIG. 26, a moth-eye film is bonded to the front surface of the polarizing plate 44 of the display unit 21 with an OCA, and an AR coating is formed on the back surface and the front surface of the protective plate 22.

Then, in FIG. 26, similarly to FIG. 17, an OCA containing a diffusion material having an AG structure is used as an adhesive for bonding the polarizing plate 44 and the glass 42 of the display unit 21.

Figure 27:
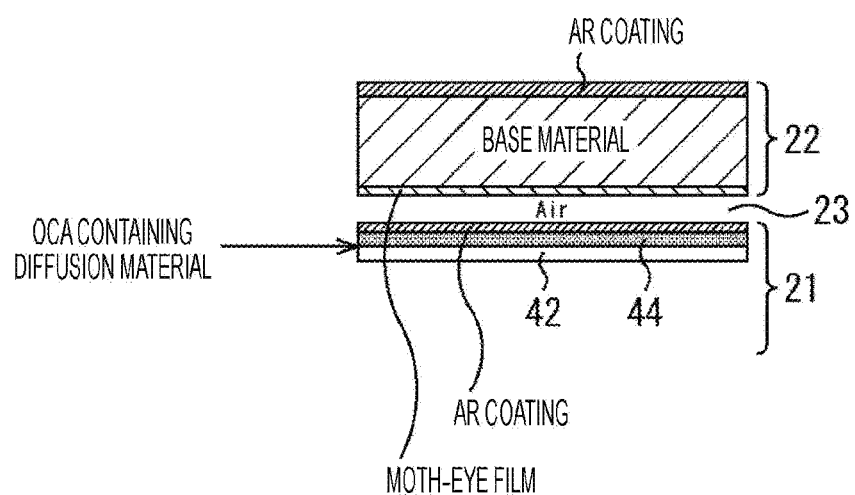
FIG. 27 is a sectional view illustrating a 22nd detailed configuration example of the display device 13.

FIG. 27 is a sectional view illustrating a 22nd detailed configuration example of the display device 13.

In FIG. 27, an AR coating is formed on the front surface of the polarizing plate 44 of the display unit 21, and a moth-eye film is bonded to the back surface of the protective plate 22 with an OCA.

Moreover, in FIG. 27, the AR coating is formed on the front surface of the protective plate 22.

Then, in FIG. 27, similarly to FIG. 17, an OCA containing a diffusion material having an AG structure is used as an adhesive for bonding the polarizing plate 44 and the glass 42 of the display unit 21.

Figure 28:
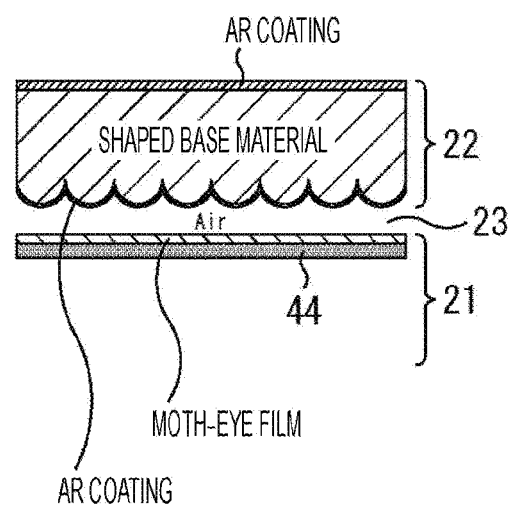
FIG. 28 is a sectional view illustrating a 23rd detailed configuration example of the display device 13.

FIG. 28 is a sectional view illustrating a 23rd detailed configuration example of the display device 13.

In FIG. 28, a moth-eye film is bonded to the front surface of the polarizing plate 44 of the display unit 21 with an OCA, and the back surface of the protective plate 22 is formed into an uneven structure having an AG structure, that is, an uneven structure having a pitch larger than a wavelength of visible light and smaller than a pixel pitch.

Then, an AR coating is formed on the uneven structure having the AG structure on the back surface of the protective plate 22.

Moreover, in FIG. 28, the AR coating is formed on the front surface of the protective plate 22.

Figure 29:
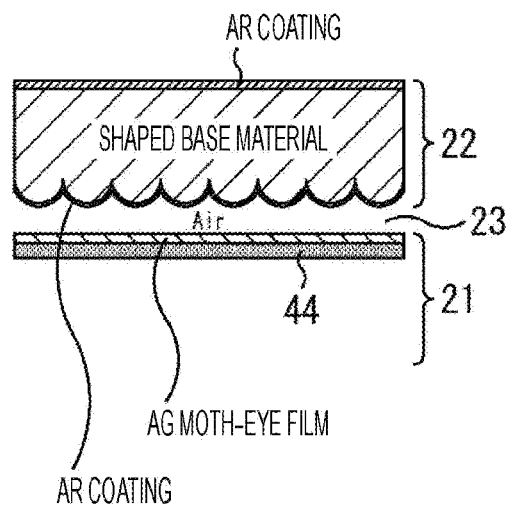
FIG. 29 is a sectional view illustrating a 24th detailed configuration example of the display device 13.

FIG. 29 is a sectional view illustrating a 24th detailed configuration example of the display device 13.

In FIG. 29, an AG moth-eye film is bonded to the front surface of the polarizing plate 44 of the display unit 21.

Moreover, in FIG. 29, similarly to FIG. 28, the back surface of the protective plate 22 has an uneven structure having an AG structure, and an AR coating is formed on the uneven structure having the AG structure.

Then, in FIG. 29, the AR coating is formed on the front surface of the protective plate 22.

Figure 30:
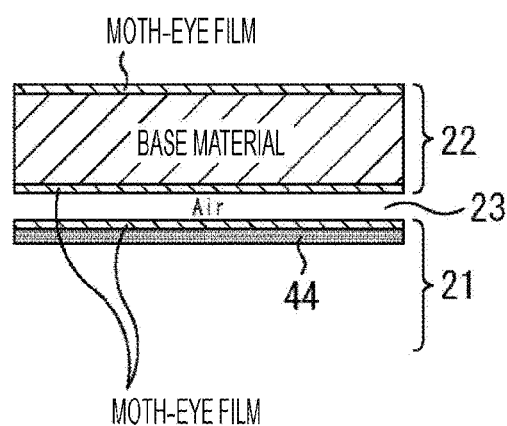
FIG. 30 is a sectional view illustrating a 25th detailed configuration example of the display device 13.

FIG. 30 is a sectional view illustrating a 25th detailed configuration example of the display device 13.

In FIG. 30, a moth-eye film is bonded to the front surface of the polarizing plate 44 of the display unit 21 and the back surface and the front surface of the protective plate 22 with an OCA.

Figure 31:
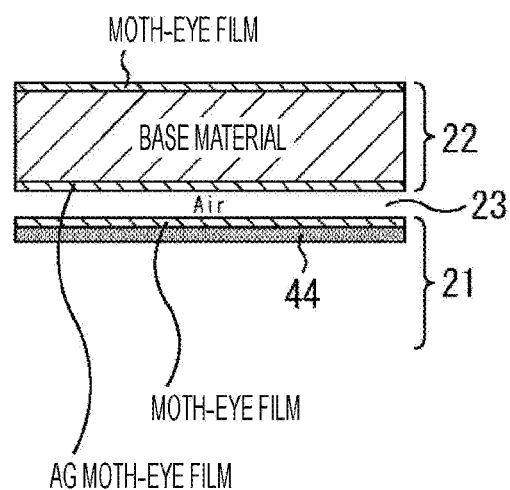
FIG. 31 is a sectional view illustrating a 26th detailed configuration example of the display device 13.

FIG. 31 is a sectional view illustrating a 26th detailed configuration example of the display device 13.

In FIG. 31, a moth-eye film is bonded to the front surface of the polarizing plate 44 of the display unit 21 with an OCA, and an AG moth-eye film is bonded to the back surface of the protective plate 22.

Moreover, in FIG. 31, a moth-eye film is bonded to the front surface of the protective plate 22 with the OCA.

Figure 32:
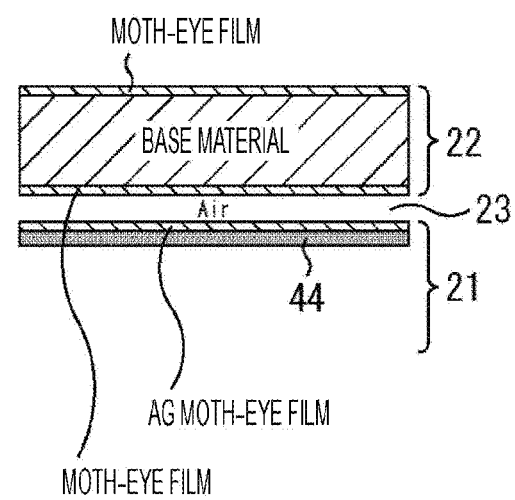
FIG. 32 is a sectional view illustrating a 27th detailed configuration example of the display device 13.

FIG. 32 is a sectional view illustrating a 27th detailed configuration example of the display device 13.

In FIG. 32, an AG moth-eye film is bonded to the front surface of the polarizing plate 44 of the display unit 21, and a moth-eye film is bonded to the back surface and the front surface of the protective plate 22 with an OCA.

Figure 33:
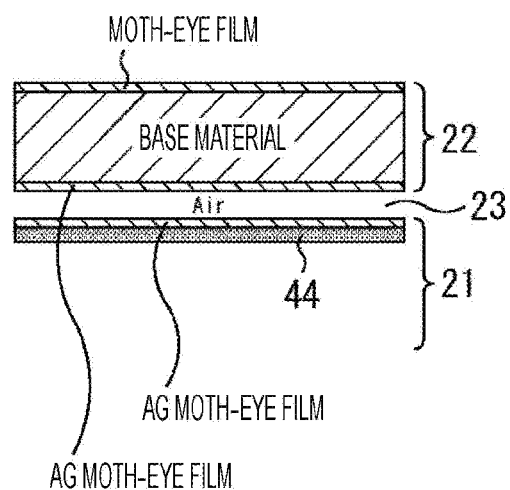
FIG. 33 is a sectional view illustrating a 28th detailed configuration example of the display device 13.

FIG. 33 is a sectional view illustrating a 28th detailed configuration example of the display device 13.

In FIG. 33, an AG moth-eye film is bonded to the front surface of the polarizing plate 44 of the display unit 21 and the back surface of the protective plate 22.

Moreover, in FIG. 33, a moth-eye film is bonded to the front surface of the protective plate 22 with an OCA.

Figure 34:
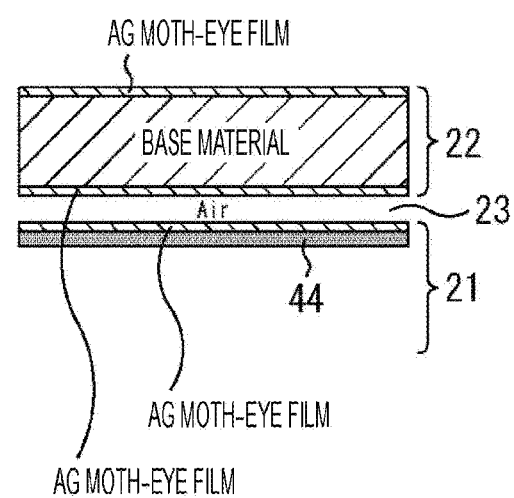
FIG. 34 is a sectional view illustrating a 29th detailed configuration example of the display device 13.

FIG. 34 is a sectional view illustrating a 29th detailed configuration example of the display device 13.

In FIG. 34, an AG moth-eye film is bonded to the front surface of the polarizing plate 44 of the display unit 21 and the back surface and the front surface of the protective plate 22.

Figure 35:
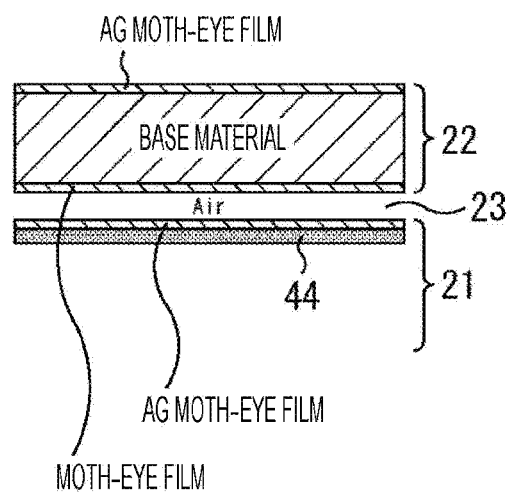
FIG. 35 is a sectional view illustrating a 30th detailed configuration example of the display device 13.

FIG. 35 is a sectional view illustrating a 30th detailed configuration example of the display device 13.

In FIG. 35, an AG moth-eye film is bonded to the front surface of the polarizing plate 44 of the display unit 21, and a moth-eye film is bonded to the back surface of the protective plate 22 with an OCA.

Moreover, in FIG. 35, the AG moth-eye film is bonded to the front surface of the protective plate 22.

Figure 36:
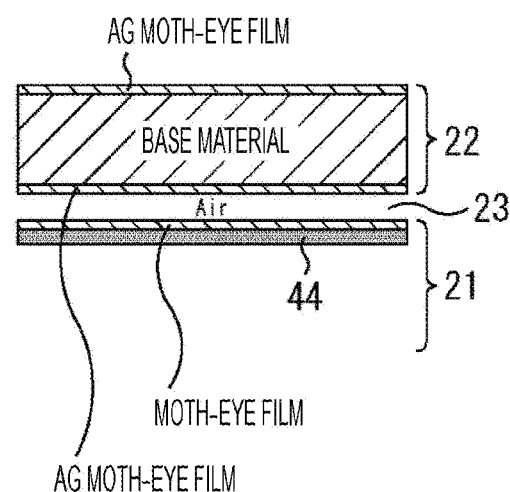
FIG. 36 is a sectional view illustrating a 31st detailed configuration example of the display device 13.

FIG. 36 is a sectional view illustrating a 31st detailed configuration example of the display device 13.

In FIG. 36, a moth-eye film is bonded to the front surface of the polarizing plate 44 of the display unit 21 with an OCA, and an AG moth-eye film is bonded to the back surface of the protective plate 22.

Moreover, in FIG. 36, the AG moth-eye film is bonded to the front surface of the protective plate 22.

Note that an embodiment of the present technology is not limited to the above-described embodiment, and various modifications can be made without departing from the scope of the present technology.

Furthermore, the effects described in the present specification are merely examples and are not limited, and there may be other effects.

Moreover, in the present specification, the system means a set of a plurality of components (devices, modules (parts), and the like), and it does not matter whether or not all the components are in the same housing. Therefore, a plurality of devices housed in separate housings and connected via a network, and one device housing a plurality of modules in one housing are both systems.

Note that the present technology can have the following configurations.

<1>

A medical observation system including:

an observation device that observes a living body of a medical treatment target;

a signal processing device that generates a biological image related to the living body by processing an output signal of the observation device; and a display device including a display unit that displays the biological image and a transparent protective plate disposed on a front surface side of the display unit, in which an uneven structure having unevenness with a pitch and a height smaller than a wavelength of visible light is formed on any one or more of a front surface side of the protective plate, a back surface side of the protective plate, and the front surface side of the display unit, and an anti-glare (AG) structure having an AG function is formed on any one or more of the front surface side of the protective plate, the back surface side of the protective plate, and the front surface side of the display unit.

<2>
The medical observation system according to <1>,
in which the AG structure is another uneven structure having unevenness with a pitch larger than the wavelength of the visible light and smaller than a pixel pitch of the display unit.

<3>
The medical observation system according to <2>,
in which one or both of a front surface and a back surface of the protective plate has/have the another uneven structure having the AG structure.

<4>
The medical observation system according to <2>,
in which a film in which the uneven structure is formed on the another uneven structure is bonded to any one or more of the front surface side of the protective plate, the back surface side of the protective plate, and the front surface side of the display unit.

<5>
The medical observation system according to any one of <1> to <4>,
in which the uneven structure is bonded to the front surface side of the display unit with an adhesive containing a diffusion material having a size smaller than a pixel pitch of the display unit and having the AG structure.

<6>
The medical observation system according to any one of <1> to <5>,
in which a polarizing plate is provided on a front surface of the display unit, and
the polarizing plate is bonded with an adhesive containing a diffusion material having a size smaller than a pixel pitch of the display unit and having the AG structure.

<7>
The medical observation system according to any one of <1> to <6>,
in which a gap is formed between the display unit and the protective plate.

<8>
The medical observation system according to any one of <1> to <7>,
in which the uneven structure includes a hydrophilic material.

<9>
The medical observation system according to any one of <1> to <7>,
in which the uneven structure includes a hydrophobic material.

<10>
The medical observation system according to any one of <1> to <9>,
in which the protective plate includes chemically strengthened glass.

<11>
A display device including:
a display unit that displays a biological image related to a living body of a medical treatment target; and
a transparent protective plate disposed on a front surface side of the display unit,
in which an uneven structure having unevenness with a pitch and a height smaller than a wavelength of visible light is formed on any one or more of a front surface side of the protective plate, a back surface side of the protective plate, and the front surface side of the display unit, and
an anti-glare (AG) structure having an AG function is formed on any one or more of the front surface side of the protective plate, the back surface side of the protective plate, and the front surface side of the display unit.

<12>
The display device according to <11>,
in which the AG structure is another uneven structure having unevenness with a pitch larger than the wavelength of the visible light and smaller than a pixel pitch of the display unit.

<13>
The display device according to <12>,
in which one or both of a front surface and a back surface of the protective plate has/have the another uneven structure having the AG structure.

<14>
The display device according to <12>,
in which a film in which the uneven structure is formed on the another uneven structure is bonded to any one or more of the front surface side of the protective plate, the back surface side of the protective plate, and the front surface side of the display unit.

<15>
The display device according to any one of <11> to <14>,
in which the uneven structure is bonded to the front surface side of the display unit with an adhesive containing a diffusion material having a size smaller than a pixel pitch of the display unit and having the AG structure.

<16>
The display device according to any one of <11> to <15>,
in which a polarizing plate is provided on a front surface of the display unit, and
the polarizing plate is bonded with an adhesive containing a diffusion material having a size smaller than a pixel pitch of the display unit and having the AG structure.

<17>
The display device according to any one of <11> to <16>,
in which a gap is formed between the display unit and the protective plate.

<18>
The display device according to any one of <11> to <17>,
in which the uneven structure includes a hydrophilic material.

<19>
The display device according to any one of <11> to <17>,
in which the uneven structure includes a hydrophobic material.

<20>
The display device according to any one of <11> to <19>,
in which the protective plate includes chemically strengthened glass.

REFERENCE SIGNS LIST

11 Observation device
12 Signal processing device
13 Display device

21 Display unit
22 Protective plate
23 Gap
31 Housing
32 Light source
33 Light guide plate
34 Optical sheet
35 Liquid crystal element
36 Bezel
41 Liquid crystal
42, 43 Glass
44, 45 Polarizing plate
51 Housing
52 Organic EL element

The invention claimed is:

1. A medical observation system comprising:
an observation device that observes a living body of a medical treatment target;
a signal processing circuit that generates a biological image related to the living body by processing an output signal of the observation device;
a display that displays the biological image; and
a transparent protective plate disposed on a front surface side of the display,
wherein
a first uneven structure having unevenness with a pitch and a height smaller than a wavelength of visible light is formed on any one or more of a front surface side of the protective plate, a back surface side of the protective plate, and the front surface side of the display,
a second uneven structure having unevenness with a pitch larger than the wavelength of the visible light and smaller than a pixel pitch of the display having an anti-glare (AG) function is formed on any one or more of the front surface side of the protective plate, the back surface side of the protective plate, and the front surface side of the display, wherein at least one of the first uneven structure and the second uneven structure is between the display and the transparent protective plate and the second uneven structure is between the display and the first uneven structure,
an air gap is formed between the display and the protective plate, and
a film in which the first uneven structure is formed on the second uneven structure includes a hydrophilic or hydrophobic material, and is located in the air gap and bonded to the front surface side of the display with an adhesive containing a diffusion material having a size smaller than the pixel pitch of the display and having an AG structure.

2. The medical observation system according to claim 1, wherein one or both of a front surface and a back surface of the protective plate has/have the second uneven structure.

3. The medical observation system according to claim 1, wherein a polarizing plate is provided on a front surface of the display.

4. The medical observation system according to claim 1, wherein the protective plate includes chemically strengthened glass.

5. A display device comprising:
a display that displays a biological image related to a living body of a medical treatment target; and
a transparent protective plate disposed on a front surface side of the display,
wherein
a first uneven structure having unevenness with a pitch and a height smaller than a wavelength of visible light is formed on any one or more of a front surface side of the protective plate, a back surface side of the protective plate, and the front surface side of the display,
a second uneven structure having unevenness with a pitch larger than the wavelength of the visible light and smaller than a pixel pitch of the display having an anti-glare (AG) function is formed on any one or more of the front surface side of the protective plate, the back surface side of the protective plate, and the front surface side of the display, wherein at least one of the first uneven structure and the second uneven structure is between the display and the transparent protective plate and the second uneven structure is between the display and the first uneven structure,
an air gap is formed between the display and the protective plate, and
a film in which the first uneven structure is formed on the second uneven structure includes a hydrophilic or hydrophobic material, and is located in the air gap and bonded to the front surface side of the display with an adhesive containing a diffusion material having a size smaller than the pixel pitch of the display and having an AG structure.

6. The display device according to claim 5, wherein one or both of a front surface and a back surface of the protective plate has/have the second uneven structure.

7. The display device according to claim 5, wherein a polarizing plate is provided on a front surface of the display.

8. The display device according to claim 5, wherein the protective plate includes chemically strengthened glass.

9. The display device according to claim 5, wherein the first uneven structure and the second uneven structure are on different ones of the front surface side of the protective plate, the back surface side of the protective plate, and the front surface side of the display.

* * * * *